United States Patent
Roach et al.

[11] Patent Number: 5,770,151
[45] Date of Patent: Jun. 23, 1998

[54] HIGH-SPEED LIQUID DEPOSITION DEVICE FOR BIOLOGICAL MOLECULE ARRAY FORMATION

[75] Inventors: David J. Roach, Los Gatos; Richard F. Johnston, Murphys, both of Calif.

[73] Assignee: Molecular Dynamics, Inc., Sunnyvale, Calif.

[21] Appl. No.: 658,527

[22] Filed: Jun. 5, 1996

[51] Int. Cl.$^6$ .................................................. G01N 35/10
[52] U.S. Cl. ........................... 422/63; 422/65; 422/100; 436/174; 436/180; 73/864.02
[58] Field of Search ................. 422/63, 65, 100; 436/43, 49, 174, 180; 73/864.01, 864.02, 864.14

[56] References Cited

U.S. PATENT DOCUMENTS

| | | | |
|---|---|---|---|
| 3,077,780 | 2/1963 | Takatsy | 422/100 |
| 3,252,331 | 5/1966 | Lancaster | 73/425.4 |
| 4,162,896 | 7/1979 | Hosli | 422/100 |
| 4,285,907 | 8/1981 | Hugemann et al. | 422/100 |
| 4,325,913 | 4/1982 | Wardlaw | 422/100 |
| 4,441,373 | 4/1984 | White | 73/864.02 |
| 4,738,669 | 4/1988 | Vlock | 604/289 |
| 4,757,437 | 7/1988 | Nishimura | 364/167 |
| 5,059,398 | 10/1991 | Kenney | 422/100 |
| 5,223,225 | 6/1993 | Gautsch | 422/100 |
| 5,230,864 | 7/1993 | Columbus | 422/100 |
| 5,322,192 | 6/1994 | Godolphin et al. | 222/83 |
| 5,324,480 | 6/1994 | Shumate et al. | 422/63 |
| 5,334,353 | 8/1994 | Blattner | 422/100 |
| 5,354,537 | 10/1994 | Moreno | 422/100 |
| 5,460,782 | 10/1995 | Coleman et al. | 422/100 |

FOREIGN PATENT DOCUMENTS

WO95/35505  12/1995  WIPO .

*Primary Examiner*—Long V. Le
*Attorney, Agent, or Firm*—Thomas Schneck

[57] ABSTRACT

A microspot deposition system featuring a hollow cylindrical wall extending from a closed end, terminating in an open end and including a longitudinal gap extending from the open end toward the closed end to allow the rapid exhaustion of the atmosphere and efficient cleaning within the cylindrical wall. The cylindrical wall defines a lumen with both the lumen and the gap adapted to facilitate capillary action of liquid in fluid communication therewith to form a meniscus proximate to the open end. To facilitate deposition of liquid contained within the lumen, the gap may be tapered so that it is narrowest proximate to the open end. The narrowed portion of the gap results in a meniscus having a reduced area to ensure preferential fluid flow toward the open end, which facilitates deposition via capillary action between the liquid in the lumen and a working surface on which the liquid is to be deposited.

16 Claims, 3 Drawing Sheets

HIGH-SPEED LIQUID DEPOSITION DEVICE FOR BIOLOGICAL MOLECULE ARRAY FORMATION

TECHNICAL FIELD

The present invention pertains to the field of biochemical analysis devices. Specifically, the present invention pertains to an improved liquid deposition device for automated deposition of biological molecules, for example, for forming a microspot array.

BACKGROUND ART

Modern research and clinical laboratory procedures include biological and chemical analysis of specimen substances that require extensive and/or numerous fluid manipulations. Many of the routine applications used for analysis are immunoassays, viral assays, protein assays, etc., which require precise quantities of reagents to be employed. Standard fluid transfer and manipulable techniques include pipetting, diluting, dispensing, aspirating and plate washing. Conventional assays may be performed, in part, by rapid manipulation of manual pipettors or conducting assays which are piecemeal automated.

U.S. Pat. No. 5,460,782 to Coleman et al. discloses a manual micropipette including, inter alia, a tubular body with an open end. The tubular body is sized to permit liquid flow by capillary action. An aperture is provided in the side wall having a diameter smaller than the diameter of the open end. The aperture allows air to escape during collection of the liquid. The end of the tubular body opposing the open end may be closed or may include a piston to facilitate collection and deposition of liquid.

U.S. Pat. No. 5,059,398 to Kenney discloses a preselected-volume capillary pipette device including, inter alia, a cylindrical tube having openings at opposed ends. One end is adapted to be an inlet and an outlet, allowing liquids to pass therethrough. Disposed in the remaining opening is a plunger of a piston. The plunger is formed so as not to completely impede air from moving between the capillary tube and the plunger. In this manner, the end of the capillary tube in which the plunger is disposed operates as a vent.

U.S. Pat. No. 5,230,864 to Columbus discloses a gravity assisted liquid collection device including, inter alia, two apertured portions connected at an intermediate point so that the apertured portions are angled with respect to one another. The first portion provides the capillary attraction through its aperture by including a channel that will facilitate capillary flow. The second portion provides gravity flow further into the device, from the intermediate point, by increasing the size of the channel to allow gravity to passively overcome any surface attraction between the channel walls and the liquid. Specifically, the inclination of this portion causes gravity to pull the liquid from the intermediate point and collect at one end of the second portion. An aperture is included in the second portion which acts as a vent.

U.S. Pat. No. 4,738,669 to Vlock discloses a hand-held fluid dispenser using capillary action which includes, inter alia, a handle portion supporting at least three spaced-apart flexible prongs, or tines, that meet at a pyramidal apex to form a liquid-containing cradle. Liquid is held within the cradle by a surface tension of the liquid with the prongs. The cradle pocket includes a capillary channel which terminates at the tip of the prongs. When the tip of the prongs is in contact with a body surface in question, they flex, allowing liquid to flow from the cradle through the channel and onto the surface.

A problem with the aforementioned devices is that manual liquid handling techniques increase the chance of inaccuracies and error. This is due, in part, to the repetitious nature of liquid handling for experiments, some of which require as much as 9000 manipulations, inherently leading to mistakes due to human error, many of which may go undetected.

To overcome the deficiencies of manual pipettes, automated pipettes were introduced. Many of the automated pipettes and micro-pipettes employ suction to facilitate collection and deposition of liquids. One such device is disclosed in U.S. Pat. No. 5,334,353 to Blattner in which a micro-pipette device is disclosed which allows a sub-microliter volume to be transferred. A built-in vacuum-based rinse station permits a user to dispense a variety of fluids without cross-contamination. Although the automated pipettes substantially decrease inaccuracies due to human error, mechanical wear often introduces additional errors and inaccuracies into the assays. For example, the amount of liquid collected by a micro-pipette may be dependent upon the vacuum present in the lumen of the same. As the gaskets in the pump wear, the vacuum level tends to fluctuate, causing quantitative variations in liquid which is collected. This often results in cross-contamination, because an insufficient amount of wash fluid may be collected so as to preclude cleansing the entire pipette. As with human-introduced errors, errors due to mechanical wear often go undetected until total mechanical failure occurs. Finally, both manual and aspirating pipettes are often slow, greatly increasing the time and cost of assaying a particular sample.

PCT publication No. WO 95/35505 discloses an automated pipette system which overcomes many of the defects associated with automated aspirating pipettes. The system includes, inter alia, a reagent dispenser having an open capillary channel which is adapted to hold a quantity of reagent. The capillary channel is formed from a pair of spaced-apart, coextensive, elongate members which are tapered toward one another, converging to a tip. The dispenser is attached to a solenoid for rapid movement along a vertical axis. The solenoid is attached to an arm that affords movement along two directions, both of which are transverse to the vertical movement of the dispenser. Typically, the arm will move the dispenser between wells containing a reagent to be collected and a substrate upon which the reagent is to be deposited. Collection is achieved by capillary action. Deposition of reagents is achieved by rapidly moving the dispenser tip toward and away from the substrate, making momentary contact against the same. In effect, the dispenser tip is tapped against the substrate. A problem with this device is that the open channel design allows greater quantities of collected reagent to evaporate before being deposited. This results in varying quantities of fluid being deposited in each spot on the substrate. The variance in the quantity of deposited reagent may be further exacerbated by the tapping effect which may cause some of the reagent to splash away from the microspot. Finally, the repeated impact between the substrate and the dispenser tip may cause premature wear of the dispenser, thereby shortening its operational life.

What is needed is a device which is capable of collecting and depositing exacting amounts of liquid for a multitude of collection and deposition procedures at very high speeds.

SUMMARY OF THE INVENTION

In accord with the present invention, an automated microspot deposition device features a tubular liquid deposition member having a hollow cylindrical wall extending from a closed end, terminating in an open end and including a longitudinal gap extending from the open end toward the closed end. This allows the rapid exhaustion of the atmosphere within the cylindrical wall as liquid is introduced therein. The cylindrical wall defines a lumen with both the lumen and the gap adapted to facilitate capillary action of liquid in fluid communication therewith to form a meniscus proximate to he open end. To facilitate deposition of liquid contained within the lumen, the gap may be tapered so that it is narrowest proximate to the open end. The narrowed portion of the gap results in a smaller, flatter meniscus and also ensures preferential fluid flow toward the open end. In this fashion, the narrowed portion of the gap facilitates deposition via capillary action between the liquid in the lumen and a working surface on which the liquid is to be deposited. The deposition device is attached to a workstation which provides robotic movement of the same in three dimensions. The work-station may be controlled by a central processing unit for automated operation.

BEST MODE FOR CARRYING OUT THE INVENTION

Figure 1:
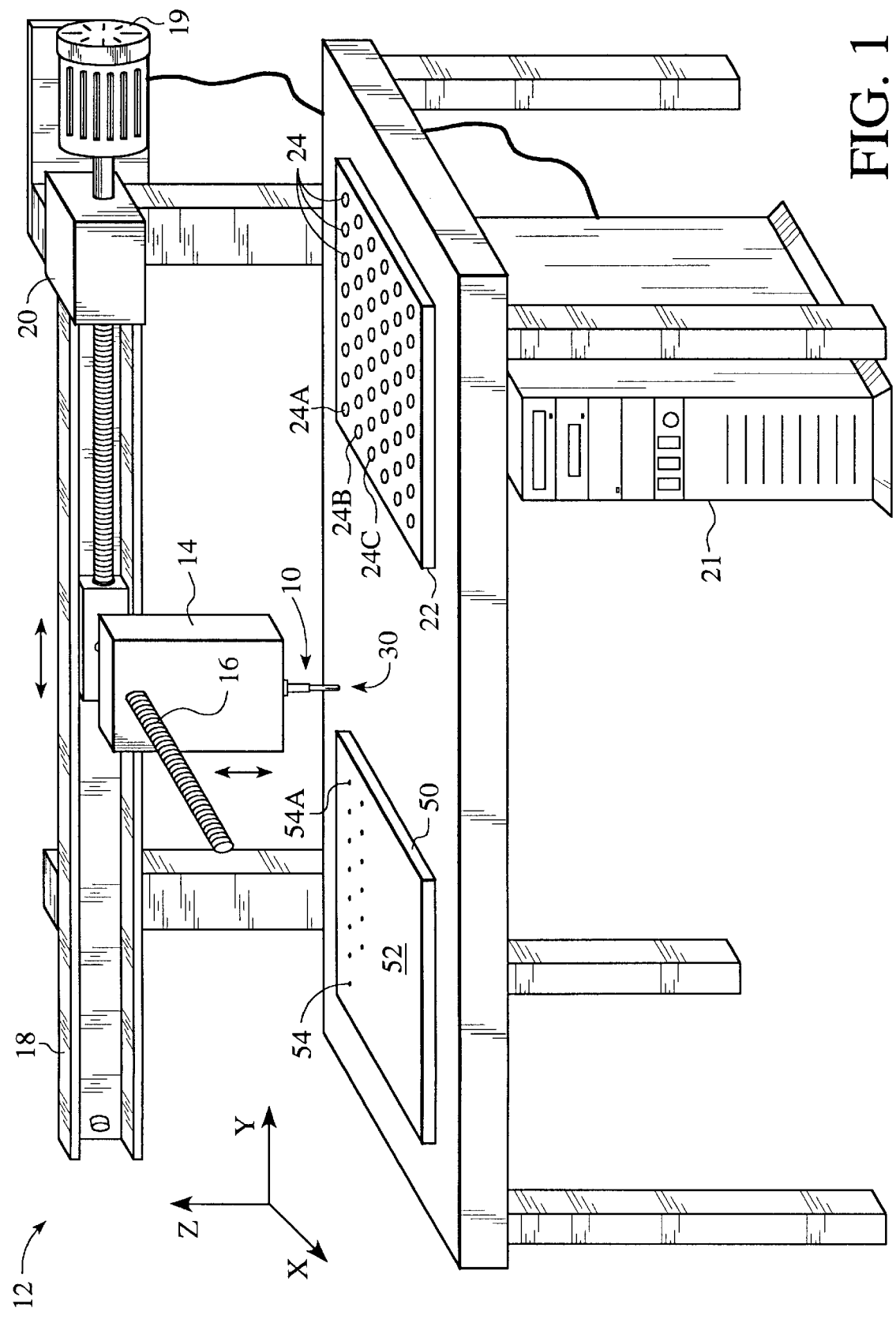
FIG. 1 is a plan perspective view of the system incorporating the present invention.

Referring to FIG. 1, a capillary collection and deposition device 10 is shown attached to a work-station 12 that may be manually controlled or automated to form, for example, a micro-array of analyte-assay regions in a substrate or porous membrane. The work-station includes a pod 14, an arm 16 and a cross-member 18. Arm 16 has a longitudinal axis extending parallel to an X axis, with pod 14 movably connected thereto. Pod 14 facilitates movement of capillary device 10 along the Z direction. Movement of capillary device 10 along the X direction is achieved by pod 14 moving along the longitudinal axis of arm 16. Movement along the Y direction is achieved by arm 16 being movably mounted to a cross-member 18, which has a longitudinal axis extending parallel to the Y direction. Pod 14, arm 16 and cross member 18 are each coupled to a motor 19 and transmission 20, which provides the necessary torque and power to move the same. Automated control of work-station 12 may be achieved via a computer 21 which may be operationally coupled to motor 19 and transmission 20.

Work-station 12 typically has a receptacle 22, such as a microtiter plate, containing one or more wells 24. For example, wells 24 may contain the analyte-specific reagents necessary to assay biological molecules, such as DNA fragments, using fluorescent labelling techniques. A first subset of wells 24 may contain specific antibodies coupled to a fluorescent dye, while a second subset of wells 24 may contain antigens. The remaining wells 44 may contain cleaning solution to prevent cross-contamination between wells containing antigens and wells containing antibodies. Alternatively, the cleaning solution may be contained in a separate open tank. A blotter may also be used.

Figure 2:
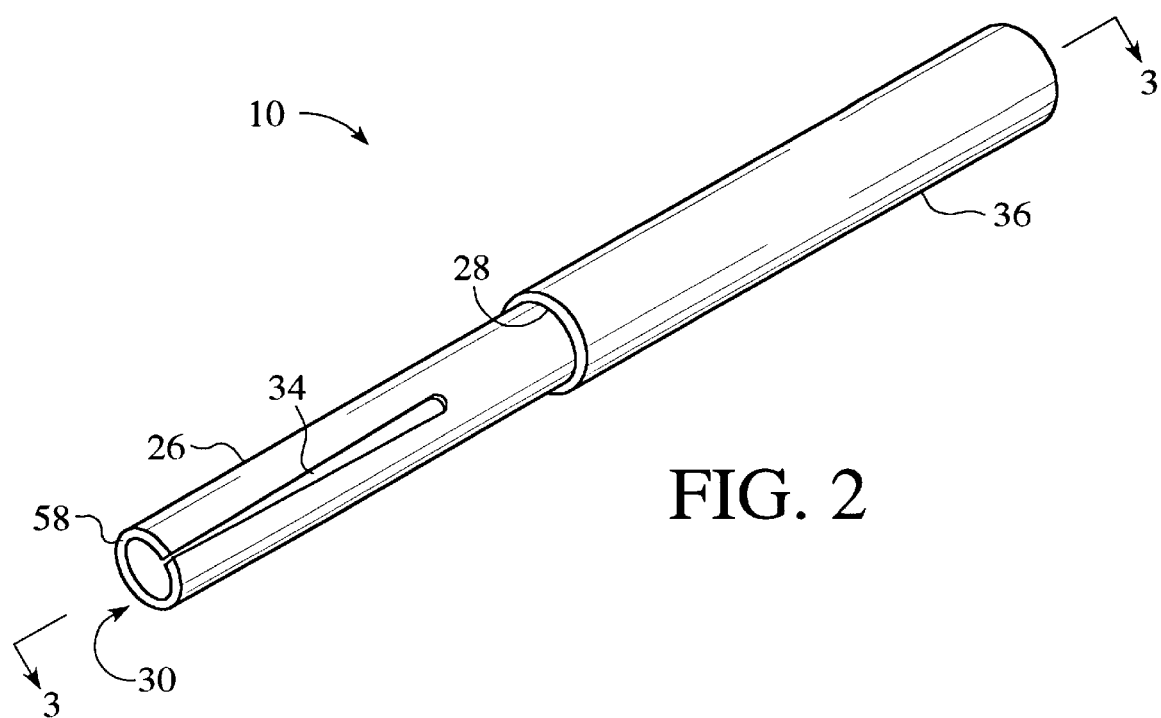
FIG. 2 is a perspective view of the invention in accord with the preferred embodiment.
Figure 3:
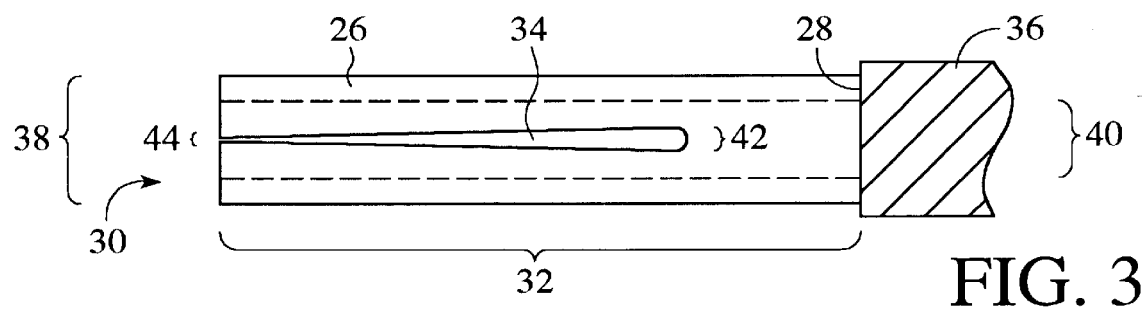
FIG. 3 is a partial cross-sectional view of the invention shown in FIG. 2, taken along lines 3—3.

With reference to both FIGS. 2 and 3, capillary device 10 includes a hollow cylindrical wall 26 extending from a closed end 28, terminating in an open end 30, defining a lumen 32 therebetween. Cylindrical wall 26 includes a longitudinal gap 34 that extends from open end 30 toward closed end 28. Disposed proximate to closed end 28, and extending away therefrom, is a rigid body portion 36. Rigid body portion 36 attaches device 10 to pod 14. Device 10 is spring loaded vertically so that a plurality of devices 10 may be attached to pod 14 and normal manufacturing tolerances accommodated. The spring force required is sufficient to ensure good contact with surface 52 of substrate 50, while avoiding impact wear on device 10 during deposition. Low impact force of device 10 to surface 51 of substrate 50 ensures long lifetime of device 10. Repeatable contact geometry between device 10 and surface 52 ensures consistent liquid deposition volumes are deposited.

The dimensions of both lumen 32 and gap 34 should facilitate collection and deposition of liquids via capillary action. To that end, cylindrical wall 26 includes an outside diameter 38 typically in the range of 0.005 to 0.10 inch. Lumen 32 has a constant, or decreasing, diameter 40, along the length of wall 26, in the range of 0.002 to 0.09 inch. A first width 42 of gap 34 as measured proximate to closed end 28 is equal to or narrower than diameter 40, measuring approximately 0.0040 inch. Capillary device 10 may be manufactured from any suitable material; for example, it may be formed of glass, metal, ceramics or one of a plurality of polymers, such as polystyrene, polypropylene acrylics, polyvinyl-chloride or polycarbonate. However, it is preferred that the entire length of cylindrical wall 26 be formed from a rigid, wettable material that resists deformation.

Figure 4:
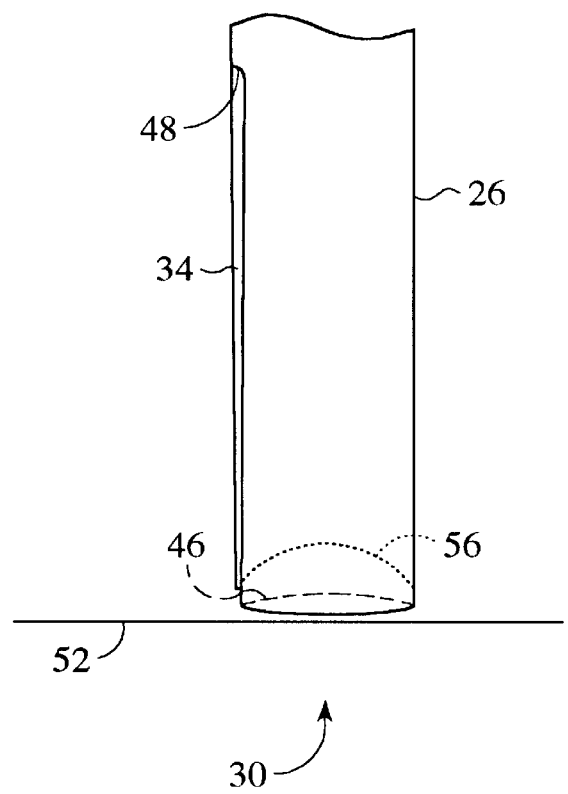
FIG. 4 is a detailed view of the invention shown in FIGS. 2–3.

Referring also to FIGS. 1 and 4, to form a micro-array, open end 30 of capillary device 10 contacts liquid in one of wells 24. Liquid moves into lumen 32 via capillary action with cylindrical wall 26, forming a meniscus 46 proximate to open end 30. Gap 34 facilitates rapid influx of liquid into lumen 32 by allowing air, present therein, to rapidly exhaust from capillary device 10 as liquid moves along cylindrical wall 26. In this fashion, the length of gap 34 defines the volume of liquid that may be contained in lumen 32. Upon reaching a termini 48 of gap 34, liquid may no longer enter the capillary device via capillary action, because the tube is plugged. The gap 34 also facilitates more efficient cleaning of the capillary device.

Upon deposition, arm 16 and cross-member 18 position capillary device 10 above a substrate 50 upon which liquid contained in the lumen 32 is to be deposited. Pod 14 moves capillary device 10 along the Z direction to allow fluid in lumen 32 to come into contact with a surface 52 of substrate 50 to form a microspot 54 of liquid thereon. To increase the deposition efficiency of capillary device 10, it is preferred that gap 34 taper proximate to open end 30 having a second width 44, measuring less than gap 42. The taper of the width of gap 34 ensures preferential fluid flow toward the open end 30. Typically, if gap 34 were not present, meniscus 56 would form in lumen 32, proximate to open end 30. As compared to meniscus 46, meniscus 56 is more concave, providing meniscus 56 with more surface area and curvature. The increased surface area and curvature reduce deposition efficiency, because a substantial portion of the fluid which forms the surface area of meniscus 56 is distally positioned from open end 30. Tapering the width of gap 34 overcomes these problems by reducing the surface area of meniscus 46, making it flatter than meniscus 56. This results from capillary forces tending to flow fluid toward an aperture with the smallest dimensions. To this end, second width 44 is typically smaller than both width 42 and the diameter of open end 30. With a flatter and smaller meniscus 46 positioned proximate to open end 30, deposition efficiency is increased.

During a collection and deposition procedure, capillary device 10 may alternately collect and deposit differing liquids contained in receptacle 42, forming a plurality of spots 54 on surface 52. In this fashion, capillary device 10 may collect a liquid containing a biological sample, e.g., antibodies, from well 24A and deposit the liquid at spot 54A. Subsequently, capillary device 10 may collect a liquid from well 24B, containing a different biological sample, e.g., antigens. To prevent cross-contamination between wells 24A and 24B, capillary device 10 may be periodically inserted into a well 24C, or a general tank, containing a wash liquid and then blotted to rapidly draw out all liquid from device 10. The deposition efficiency allows the process to maintain cross-contamination below 1 part per 1000. The deposition efficiency in part is due to gap 34. Narrowing gap 34 allows a strong capillary attraction to develop between the liquid in lumen 32 and the blotter (not shown), which removes from capillary device 10 essentially all of the liquid contained therein. In addition to narrowing gap 34, as discussed above, cross-contamination is further reduced by ensuring that cylindrical wall 26 is free of burrs. Also, providing a periphery 58 of open end 30 that forms a sharp corner with respect to cylindrical wall 26 reduces cross-contamination by increasing deposition efficiency. By substantially reducing the periodicity of inserting capillary device 10 into a wash liquid, the number of collection and deposition sequences per unit time is increased.

Figure 5:
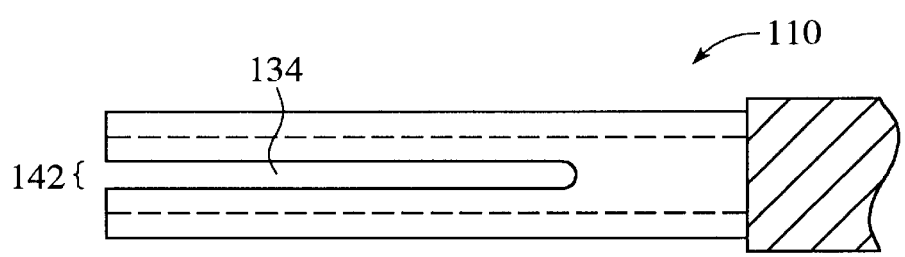
FIG. 5 is a partial cross-sectional view of a first alternate embodiment of the invention shown in FIG. 3.

Referring also to FIG. 5, a first alternate embodiment of the capillary device 10 shown in FIG. 1 is described. Capillary device 110 is similar in all respects except that gap 134 has a width 142 which is constant along its entire length.

Figure 6:
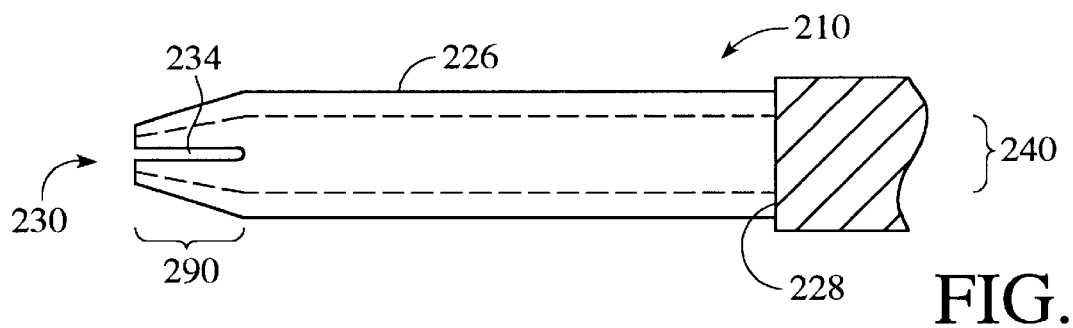
FIG. 6 is a partial cross-sectional view of a second alternate embodiment of the invention shown in FIG. 3.

With reference to FIG. 6, a second alternate embodiment of the capillary device 10 shown in FIG. 1 is described. Capillary device 210 is similar in all respects except that cylindrical wall 226, proximate to open end 230, tapers inwardly, forming a frusto-conical portion 290. Frusto-conical portion 290 is typically coextensive with gap 234, having a length in the range of 0.10 to 0.40 inch. In this fashion, inner diameter 240 tapers so that it is widest proximate to closed end 228 and narrowest proximate to open end 230. Gap 234 may also narrow along its length toward open end 230.

Figure 7:
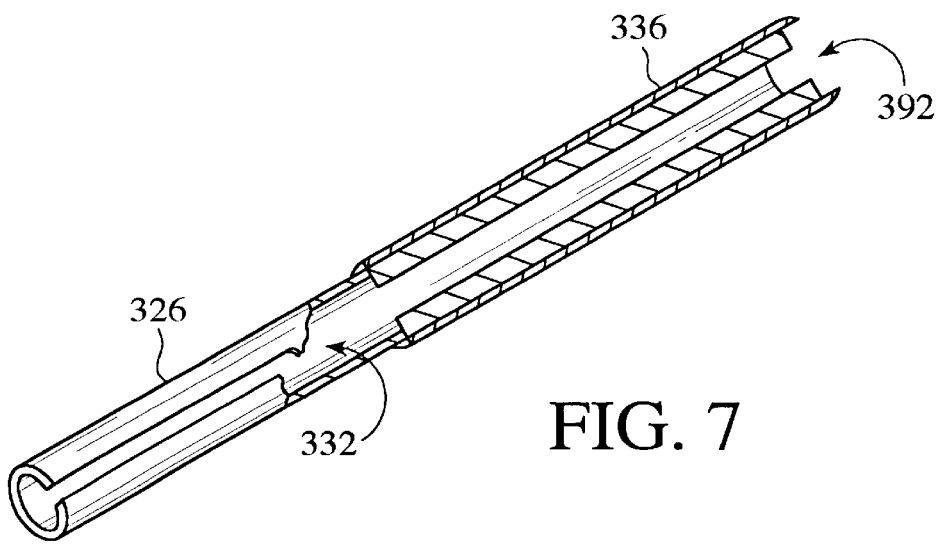
FIG. 7 is a partial cross-sectional view of a third alternate embodiment of the invention shown in FIG. 3.

Referring also to FIG. 7, shown is an alternate embodiment of the rigid body portion 36 discussed above with respect to FIG. 1. The rigid body portion 336 may include a channel 392 centrally disposed therein. In this fashion, an aspirating means such as a pump (not shown), may be placed in fluid communication with lumen 332. The aspirating means could be used to facilitate the capillary action of the cylindrical wall 326, as well as decrease deposition time of the device 310.

We claim:

1. A collection and deposition device, comprising:
   a hollow tube including an open end and a closed end disposed opposite to said open end, defining a lumen therebetween having a longitudinal axis, said tube including an elongated slit extending from said open end toward said closed end, parallel to said axis, with said lumen and said slit adapted to permit liquid flow into said tube by capillary action, the slit tapering from a wider dimension distal to the open end to a smaller dimension proximate to the open end;
   a cross-member extending along a first direction;
   an arm extending along a second direction, transverse to said first direction, with said arm movably attached to said cross-member to traverse parallel to said first direction; and
   a pod movably attached to said arm to traverse along said second direction and along a third direction, traverse to both said first and second directions, said hollow tube being mounted to said pod with said longitudinal axis extending parallel to said third direction allowing collection and deposition of liquids by providing three-dimensional movement of said hollow tube.

2. The device of claim 1 further including a drive means for providing power to move said cross-member, said arm and said pod.

3. The device of claim 1 further including a drive means for providing power to move said cross-member, said arm and said pod, and means for providing automated control to said drive means.

4. The device as recited in claim 1 further including a rigid body portion positioned proximate to said closed end.

5. The device as recited in claim 1 wherein said hollow tube has a cylindrical cross-section, with said lumen having a length and a diameter being constant along said length.

6. The device as recited in claim 1 wherein said hollow tube has a cylindrical cross-section, with said lumen having a length and a diameter, said diameter being smallest proximate to said open end and greatest proximate to said closed end.

7. The device as recited in claim 1 wherein said hollow tube comprises a rigid wall extending between said closed and open ends.

8. The device as recited in claim 1 further including a rigid body portion positioned proximate to said closed end, said rigid body portion having a channel extending completely therethrough, parallel to said axis, with said channel being in fluid communication with said lumen.

9. A collection and deposition device, comprising:
   a hollow cylindrical wall extending from a closed end, terminating in an open end, defining a lumen therebetween, said cylindrical wall including a longitudinal gap extending from said opening toward said closed end with said gap and said lumen both being adapted to facilitate capillary action of liquid in fluid communication therewith to form a meniscus proximate to said open end,
   said gap having a width which is smaller proximate to said open end than said width proximate to said closed end.

10. The device as recited in claim 1, further including a rigid body portion positioned proximate to said closed end.

11. The device as recited in claim 1 wherein said hollow tube has a cylindrical cross-section, with said lumen having a length and a diameter, said diameter being smallest proximate to said open end and greatest proximate to said closed end.

12. The device as recited in claim 11 further including means for moving said hollow cylindrical wall in three dimensions, with said hollow cylindrical wall being attached to said moving means.

13. The device as recited in claim 12 further including a rigid body portion positioned proximate to said closed end, said rigid body portion having a channel extending completely therethrough, parallel to said axis, with said channel being in fluid communication with said lumen.

14. A collection and deposition device, comprising:

a rigid body having a hollow cylindrical wall extending therefrom terminating at a closed end at one end proximate to the rigid body and in an open end opposite the closed end, the volume between the closed and open ends defining a lumen, said cylindrical wall including a slit defining a longitudinal gap extending from said open end toward said closed end with said gap and said lumen both being adapted to facilitate capillary action of liquid in fluid communication therewith to form a meniscus proximate to said open end, the slit tapering from a wider dimension proximate to the closed end to a smaller dimension proximate to the open end.

15. The device as recited in claim 14 wherein said rigid body has a length, with a diameter being constant along said length.

16. The deposition device as recited in claim 15 wherein said rigid body portion includes a channel extending completely therethrough, parallel to said axis, with said channel being in fluid communication with said lumen.

* * * * *